(12) United States Patent
Muldner

(10) Patent No.: US 6,277,128 B1
(45) Date of Patent: Aug. 21, 2001

(54) SKIN ABRASION TREATMENT DEVICE

(76) Inventor: J. Scott Muldner, 4796 Longly La., Reno, NV (US) 89502

( * ) Notice: Subject to any disclaimer, the term of this patent is extended or adjusted under 35 U.S.C. 154(b) by 0 days.

(21) Appl. No.: 09/351,230

(22) Filed: Jul. 11, 1999

Related U.S. Application Data

(60) Provisional application No. 60/092,460, filed on Jul. 11, 1998.

(51) Int. Cl.$^7$ .................................................. A61B 17/50
(52) U.S. Cl. ........................................... 606/133; 606/131
(58) Field of Search ..................................... 606/131, 132, 606/133

(56) References Cited

U.S. PATENT DOCUMENTS

| | | |
|---|---|---|
| 2,608,032 | 8/1952 | Garver . |
| 2,921,585 | 1/1960 | Schumann . |
| 3,574,239 | 4/1971 | Sollerud . |
| 3,715,838 | 2/1973 | Young et al. . |
| 4,375,740 | 3/1983 | Brown . |
| 4,482,322 | 11/1984 | Hain et al. .............................. 433/88 |
| 4,560,373 | 12/1985 | Sugino et al. .......................... 604/30 |
| 4,646,480 | 3/1987 | Williams . |
| 4,671,867 | 6/1987 | Battie et al. ............................. 209/3 |
| 4,676,749 | 6/1987 | Mabille .................................. 433/88 |
| 4,757,814 | 7/1988 | Wang et al. . |
| 4,765,099 | 8/1988 | Tanner . |
| 5,037,431 | * 8/1991 | Summers et al. ..................... 606/131 |
| 5,037,432 | 8/1991 | Molinari ................................ 606/131 |
| 5,100,412 | 3/1992 | Rosso .................................... 606/131 |
| 5,207,234 | * 5/1993 | Russo .................................... 606/131 |
| 5,309,683 | 5/1994 | Hockett . |
| 5,460,604 | * 10/1995 | Arnett et al. .......................... 606/131 |
| 5,547,376 | 8/1996 | Harrel ................................... 433/116 |
| 5,765,759 | 6/1998 | Bruns et al. .......................... 239/398 |
| 5,810,587 | 9/1998 | Bruns et al. ............................. 433/88 |
| 5,810,842 | 9/1998 | Di Fiore et al. ...................... 606/131 |
| 6,039,745 | * 3/2000 | Fiore et al. ............................ 606/131 |

FOREIGN PATENT DOCUMENTS

| | | |
|---|---|---|
| 3421390 | 12/1985 | (DE) . |
| 234608 | 4/1986 | (DE) . |
| 0258901 | 3/1988 | (EP) . |
| 553076 | 12/1956 | (IT) . |
| 1184922 | 10/1987 | (IT) . |

* cited by examiner

Primary Examiner—Paul J. Hirsch
(74) Attorney, Agent, or Firm—Carol D. Titus; James J. Leary

(57) ABSTRACT

A nozzle with an abrasion chamber for removal of the outermost layer of skin and the skin treatment system for use therewith. The abrasive material flows across a slot formed in the abrasion chamber. The path of the abrasive material may be generally helical. In the preferred helical embodiments, the paths are either vertically or horizontally oriented within the abrasion nozzle. To promote the spiral path of the material, some embodiments feed the abrasive material into the abrasion chamber at an angle causing the material to flow down the curved sidewall of a generally cylindrical abrasion chamber, thereby encouraging the spiral path.

8 Claims, 6 Drawing Sheets

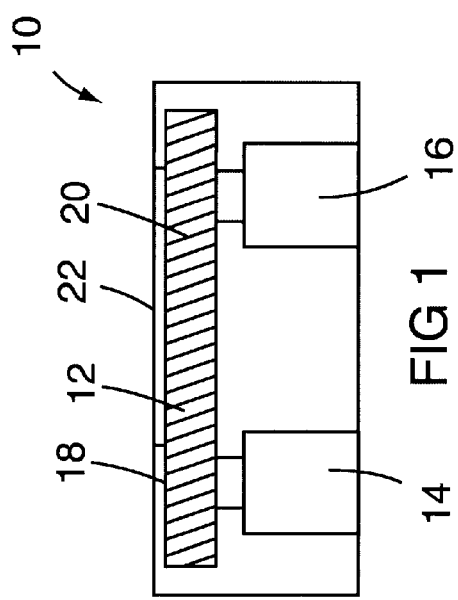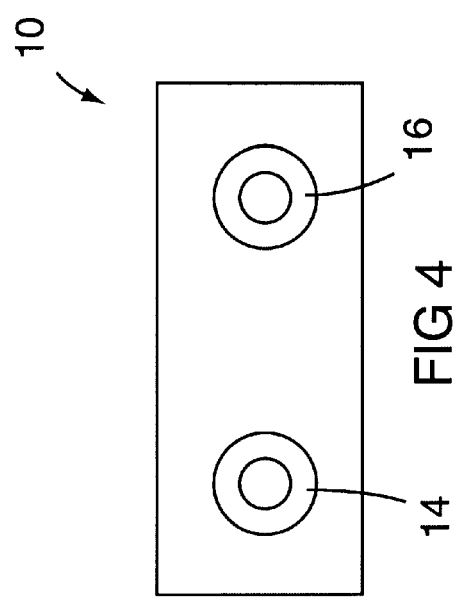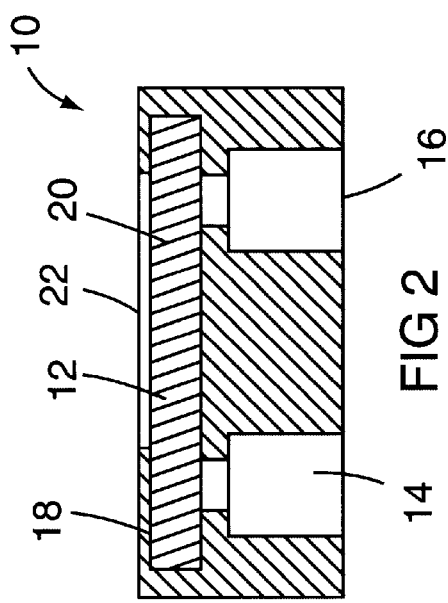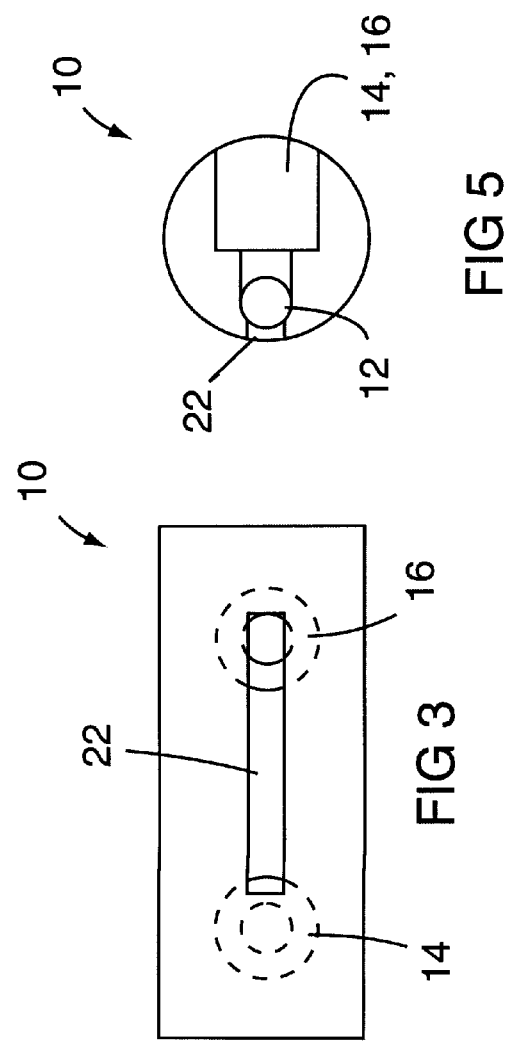

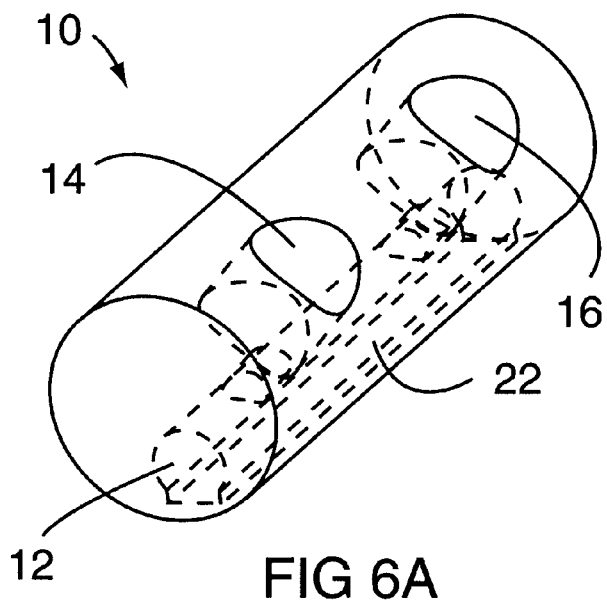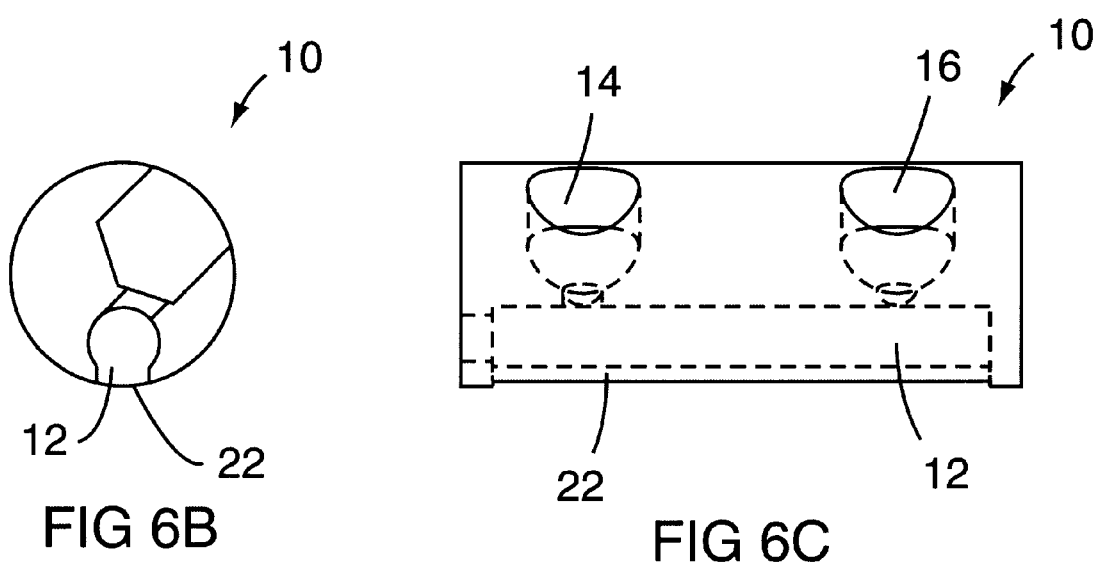

SKIN ABRASION TREATMENT DEVICE

CROSS REFERENCE TO OTHER APPLICATIONS

This application claims the benefit of U.S. Provisional Patent Application No. 60/092,460 filed Jul. 11, 1998, which is hereby incorporated by reference in its entirety.

FIELD OF INVENTION

The present invention relates generally to abrasion devices for removing surface material. More particularly, it relates to an abrasion device for removing the surface of the human tissue, particularly the skin, having an abrasion chamber with a slot through which an abrasive material passes to abrade a surface. In some embodiments, the abrasive material flows in a generally helical, spiral, or vortex path.

BACKGROUND OF THE INVENTION

The removal of the exterior surface of the skin has been used to provide softer skin for years. Typically, this has taken the form of a scrub which a user may apply to the a portion of the body, frequently the face, and the scrub material is rubbed around on the skin abrading off the outermost layer of skin cells. The user then rinses off both the scrub and the removed skin tissue.

In today's society, removal of the outer layer of skin tissue has become widely used. Application of this type of treatment is used to fade and sometimes even remove scars, stretch marks, and other blemishes on the skin, to decreases the appearance of wrinkles and other sign of aging, etc.

As our society has more and more of a desire to have smooth, clear, young-looking skin, the demand for systems to perform the removal of the outer layer of skin will increase. To achieve the desired results, the systems need to work easily, safely and effectively.

SUMMARY OF THE INVENTION

The present invention takes the form of a nozzle with an abrasion chamber for removal of the outermost layer of skin and the skin treatment system for use therewith. The abrasive material flows across a slot formed in the abrasion chamber. The path of the abrasive material may be generally helical. In the preferred helical embodiments, the paths are either vertically or horizontally oriented within the abrasion nozzle. To promote the spiral path of the material, some embodiments feed the abrasive material into the abrasion chamber at an angle causing the material to flow down the curved sidewall of a generally cylindrical abrasion chamber, thereby encouraging the spiral path. Other objects and advantages of the invention will no doubt occur to those skilled in the art upon reading and understanding the following detailed description along with the accompanying drawings.

BRIEF DESCRIPTION OF THE DRAWINGS

FIG. 1 shows a side view of the first embodiment of the abrasion nozzle.

FIG. 2 shows a cross-sectional view of the abrasion nozzle of FIG. 1.

FIG. 3 shows a top view of the abrasion nozzle of FIG. 1.

FIG. 4 shows a back view of the abrasion nozzle of FIG. 1.

FIG. 5 shows an end view of the abrasion nozzle of FIG. 1.

FIGS. 6A–C show a perspective, a cross-sectional and a side view of a second embodiment of the abrasion nozzle.

DETAILED DESCRIPTION OF THE INVENTION

Figure 7:
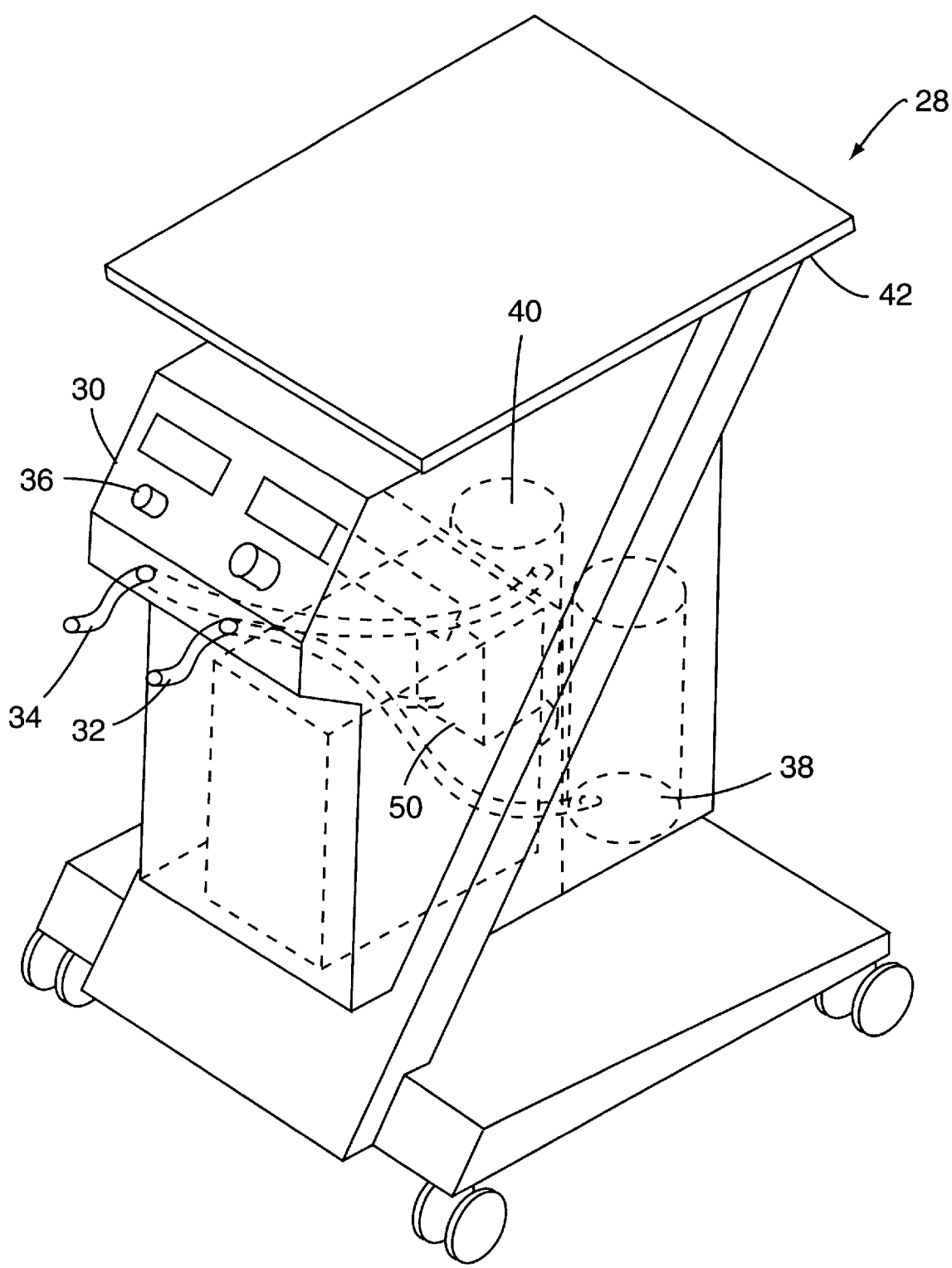
FIG. 7 shows a perspective view of the control unit for the abrasive system.

FIG. 1 shows a side view, FIG. 2 a cross-sectional view, FIG. 3 a top view, FIG. 4 a back view and FIG. 5 an end view of the first embodiment of the abrasion nozzle 10. The first embodiment of the skin abrasion nozzle 10 has an abrasion chamber 12, an inlet opening 14 leading into the abrasion chamber 12, and an outlet opening 16 through which the abrasive material and removed tissue material exit the abrasion chamber 12. Although not required, the inlet opening 14 is stepped or tapered to a smaller size to increase the velocity of the material flowing into the abrasion chamber 12. The outlet opening 16 may also be tapered or stepped outward to decrease the velocity of the material leaving the abrasion chamber 12. Reducing the velocity at which the abrasive material flows through the outer portion of the inlet opening 14 and outlet opening 16 and throughout the portions of the device other than the abrasion chamber 12, decreases the abrasion of the openings 14, 16, the tubing 32, 34 leading to and from the openings 14, 16, and the other portions of the device in contact with the abrasive material, thereby increasing the expected life of these parts.

The abrasion chamber 12 shown is generally cylindrical with sidewalls 18 having generally helical or spiral grooves and/or ridges 20. When the abrasive material enters the abrasion chamber 12 through the inlet opening 14, the material is guided to flow in a generally helical or spiral path by the grooves 20. The material continues to follow the spiral path as it progresses along the abrasion chamber 12 towards the outlet opening 16. Offset from the inlet opening 14 is a slot 22 in the abrasion chamber 12. When the material reaches the slot 22, the material is generally steadily flowing in its helical path, and flows across the slot 22. A skin surface placed against the slot 22 will be abraded by the abrasive material as it flows past. At or near the other end of the abrasion chamber 12 is an outlet opening 16 through which the abrasive material and whatever other materials have been removed from the skin surface are collected and drawn out.

For the most abrasive action, the spiral grooves 20 should spiral at relatively shallow angle, thereby causing the highest number of passes of the abrasive material across the slot 22. For applications where a slightly steeper groove angle is acceptable or desired, two or more spirals may be entwined and travel across the nozzle 12 in a configuration similar to threading for a screw.

If preferred, the abrasion chamber 12 may have generally smooth interior walls. With the smooth walls, the abrasive material may flow from one end of the abrasion chamber 12 directly to the other end following a generally U-shaped path. The abrasive material is then flowing in a line generally parallel to the slot 22.

In embodiments utilizing the spiral flow of abrasive material, the inlet opening 14 may be located at an angle to the slot 22 in the abrasion chamber 12 as shown in FIGS.

6A–C. The angled inlet opening 14 causes the abrasive material and carrier material, frequently air, to flow down the curved sidewall 18 of the abrasion chamber 12 and encourages the materials to begin a spiral path. The range of angle could be anywhere from 0 degrees (seen in FIGS. 1–5), pointing to the slot 22, which would not provide an urging towards a spiral path, to 90 degrees, pointed perpendicular to the slot 22, or more. Although not preferred, the inlet opening 14 could even be 180 degrees offset, pointing directly away from the slot 22. To encourage to spiral path the angle between the slot 22 and the inlet opening 14 may be any angle between more than 0 degrees and less than 180 degrees. The angle is preferably between 5 degrees and 175 degrees, more preferably between 15 and 90 degrees and most preferably between 30 degrees and 60 degrees. The angle shown is approximately 45 degrees. The angled inlet opening 14 may be used with either the smooth walled abrasion chambers 12 or the abrasion chambers 12 having the spiral grooves 20.

The abrasion nozzle 10 is connected to a control unit 30, shown in FIG. 7, by the inlet tube 32 and the outlet tube 34, these tubes 32, 34 are preferably formed of a flexible material so that the nozzle 10 may be easily manipulated to move the slot 22 over the skin surface to be treated. Alternate embodiments may use a more rigid system 28 if the patient being treated is manipulated instead of the nozzle 10. The tubes 32, 34 are also preferably formed of a material which does not react or quickly abrade when exposed to the abrasive material which is to be used. The control unit 30 may have controllers 36 for different settings for the unit. The controllers 36 may include, but are not required or limited to controlling the amount of material which flows through the system 28, the pressure within the system 28, etc. If the system 28 is using air to carry the abrasive material, the amount of material flowing into the system 28 may be controlled by controlling the amount of air entering the system 28. For a vacuum system 28, typical pressures and material flow rates for a dermatological application are in the range of 0–20 inches of mercury and 0–3 cubic feet per minute. For other applications and/or size of device, these values may vary significantly. The only limitation is that the abrasive material must be of a size able to flow into the slot 22 to reach the surface to be abraded and/or able to flow in a spiral, corkscrew, or vortex type of path. The control unit 30 may also display the actual values for pressure, flow, etc. by liquid crystal displays, LED's, gauges, etc. The control unit 30 may also contain a source chamber 38 for the abrasion material to be used and a material collection chamber 40 for the abrasion material and surface material abraded from the surface of the patient. If desired, the control unit 30 may be placed on a wheeled cart 42 or other movable object if it is desired to move the system 28. Alternately, the system 28 may be hard wired into a medical office in cases where the patient will visit the office, or wired into a vehicle if the system 28 will travel in a mobile vehicle, etc.

The system 28 is preferably driven by placing a vacuum source on the outlet side of the system 28. If the system 28 is set in this configuration, the abrasive material will only be drawn from the source chamber 38 when the slot 22 is placed tightly against an object, thereby completing the vacuum path. When the slot 22 is exposed to the general atmosphere, air will be drawn through the slot 22. At this point, there is insufficient vacuum pressure to drawn abrasive material from the source chamber 38. When the slot 22 is place near an object, the vacuum will tend to form a seal by drawing in a resilient object or sealing to a rigid object.

Once the vacuum is complete, abrasive material will be drawn from the source chamber 38 through the inlet tubing 32 to the inlet opening 14. From the inlet opening 14, the material will flow through the abrasion chamber 12 and abrade the skin surface exposed through the slot 22 as described above. The material will then flow through the outlet opening 16 to the outlet tubing 34 and to the collection chamber 40. The system 28, as described, forms a closed loop which recovers virtually all of the abrasive material and the surface tissue abraded off of the patient being treated, thereby reducing or eliminating the amount of contaminates which enter the atmosphere during use of the system 28. For some applications, keeping the environment sterile may be required for health issues, and for virtually all applications having a closed loop system means less or no cleanup other than removal of the material in the collection chamber 40. Alternate systems may also contain a separating mechanism which would separate the abrasive material from the surface material removed from the patient and allow the abrasive material to be reused or sterilized and reused.

The embodiment shown in FIG. 7 has an optional abrasion material injection system 50. The injection system 50 is connected to the inlet side of the system 28 and injects an quantity of abrasion material into the abrasive system 28. The injection system 50 may use a quantity of the carrier material to carry the abrasive material into the abrasion system 28. Alternately, the material itself may be placed or propelled into the flow stream of the carrier material, thereby causing the carrier material to carry the abrasive material to the nozzle 10. The injection system 50 may be used with either closed or open systems.

Alternate embodiments may use air pressure above standard atmospheric pressure to drive the system. This type of system would preferably be used in applications where collection and/or disposal of the abrasive material and/or abraded surface tissue material is handled by a separate system or is not necessary for the particular application.

Figure 8A:
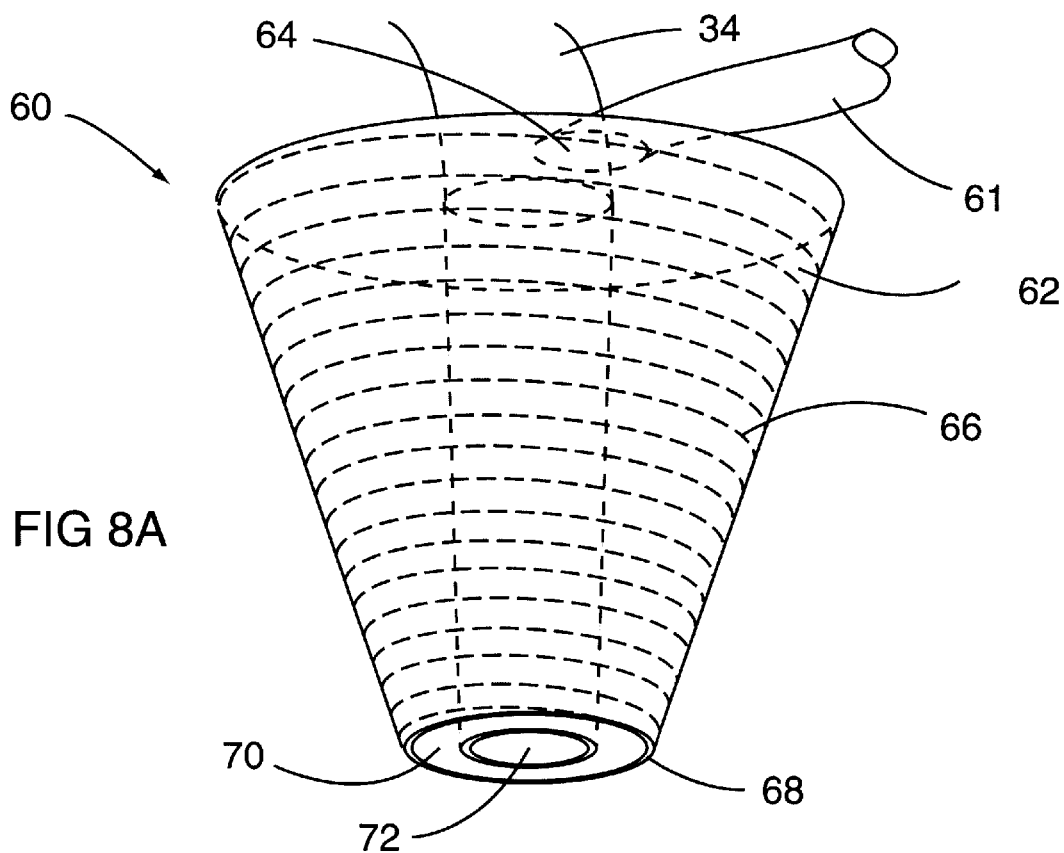
FIGS. 8A & 8B show side and top views of a third embodiment of the nozzle.
Figure 8B:
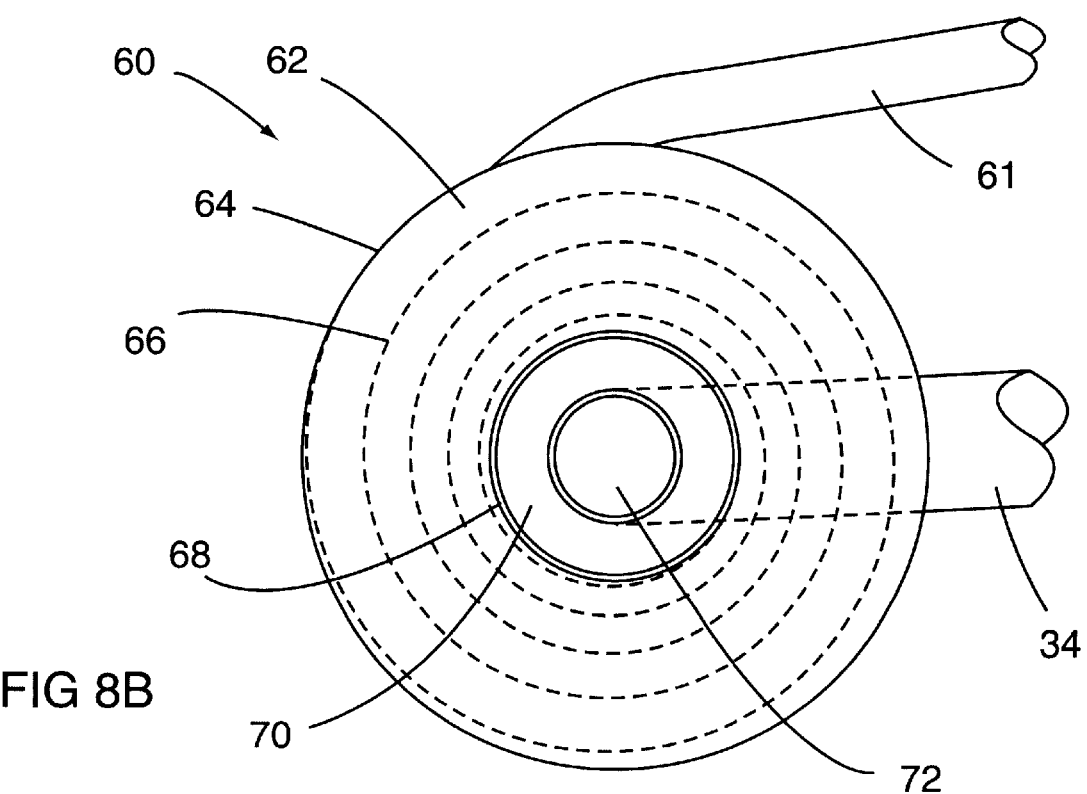

FIGS. 8A and B show a third embodiment of the abrasion nozzle 60. The third embodiment 60 uses a vertically-oriented vortex-shaped material flow within the abrasion nozzle 60. In this case, the material inlet 61 is created by feeding the material into the upper portion 62 of a generally conical nozzle 60 near the edge 64. Grooves 66 running generally laterally and slightly downward lead the abrasive material to flow around and down the perimeter of the conical nozzle 60 forming a vortex. The base 68 of the nozzle 60 has an opening 70. The base of the vortex of abrasive material touches the patient's skin through the opening 70. The outlet 72 for the material is a generally vertical channel 72 running up through the center of the nozzle 60. The outlet 72 may taper outwards as it moves up the nozzle 60 to decrease the velocity of the material moving though the outlet channel 72. The inlet 61 may also be modified to increase the velocity of the material as it flows into the nozzle 60.

Figure 9A:
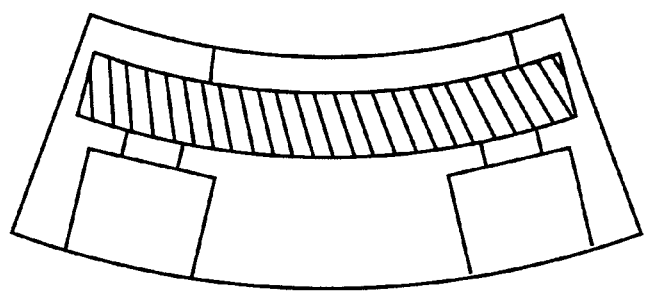
FIGS. 9A–9C show alternately shaped.
Figure 9B:
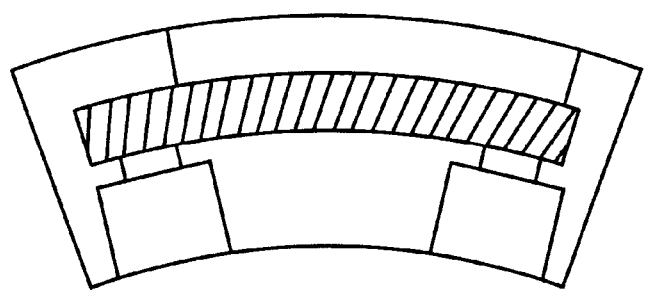
Figure 9C:
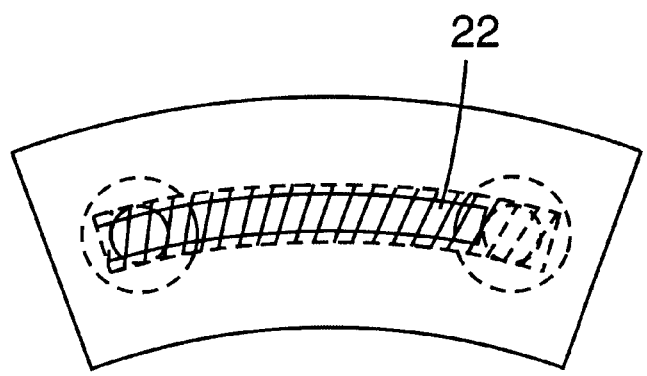

Alternate embodiments may use a combination of the vertical and horizontal abrasion systems. For example, the horizontal abrasion chamber could be conical forming a horizontal vortex, or the cylindrical abrasion chamber may be oriented vertically, angled, or even contoured, within the nozzle. The shape and configuration of flow of material through the nozzle may be adjusted to fit the particular application desired. For example, FIG. 9A shows a side view of a concave nozzle; FIG. 9B shows a side view of a convex nozzle; and FIG. 9C shows a back view of a curved nozzle.

Although any appropriate material may be used, and materials for abrasion vary for different applications, currently air is used as a carrier material to move aluminum oxide as the abrasive material. Also, wet or fluid applications may be desired for alternate embodiments. In these cases, the fluid in the system may carry the abrasive material, or the fluid itself may act as the abrasive.

The nozzle 10, 60 may be made of any material which will resist abrasion by the abrasive material. Depending on the intended application, the longevity of the nozzle 10, 60 may vary. For example, the nozzle 10, 60 may be formed of an inexpensive and softer material which is disposed of after each patient. In this case, the inlet tube 32 and outlet tube 34 are removed from the inlet opening 14 and outlet opening 16 to remove and replace the nozzle 10, 60 in the system 28. Alternately, if a more durable material is used, the nozzle 10, 60 could be sterilized or otherwise cleaned for multiple uses.

Alternate embodiments of the nozzle 10, 60 may be made of flexible materials, which would allow the user to form the slot 22 to the surface being treated by pressing the nozzle 10, 60 against the patient's skin. Other embodiments may be formed of a semi-rigid material, which would allow the user to form the nozzle 10, 60 into a particular shape prior to applying the nozzle 10, 60 to the patient. This version would also allow the user to adjust the nozzle 10, 60 during use for the different contours on the various part of the patient's body without putting undue pressure on the patient's skin.

The dimensions of the abrasion nozzle 10, 60 may vary depending on the size and shape of the part of the body being treated. However, in the current embodiment, the length of the abrasion nozzle 10, 60 is preferably in the range of 0.25 inches to 6.0 inches, more preferably in the range of 0.5 inches to 3.0 inches and most preferably in the range of 1.0 inches to 2.0 inches. The length of the abrasion nozzle 10 shown is 1.25 inches. The diameter of the abrasion nozzle 10 is preferably in the range of 0.1 inches to 2.0 inches, more preferably in the range of 0.25 inches to 1.5 inches and most preferably in the range of 0.25 inches to 0.75 inches. The embodiment shown has a diameter of 0.5 inches. The diameter of the abrasion chamber 12 is preferably in the range of 0.05 inches to 1.0 inches, more preferably in the range of 0.1 inches to 0.5 inches and most preferably in the range of 0.1 inches to 0.25 inches. The diameter of the inlet opening 14 and outlet opening 16 may differ from one another and are preferably in the range of 0.5 inches to 1.0 inches, more preferably in the range of 0.125 inches to 0.75 inches and most preferably in the range of 0.125 inches to 0.375 inches. The embodiment shown has a diameter of 0.25 inches. The optional taper (FIGS. 6A–C) or step (FIGS. 1–5) shown decreases the diameter of the inlet opening 14 by approximately half, thereby significantly increasing the speed of the abrasive material as it enters the abrasion chamber 12. The optional taper or step of the outlet opening 16 increases the diameter approximately a factor of two, thereby significantly decreasing the speed of the abrasive material as it exits the abrasion chamber 12. The amount of taper or step or the number of steps may be varied to achieve different velocities. The width of the slot 22 may be slightly smaller than the diameter of the abrasion chamber 12, as in the embodiments shown. In other embodiments, the slot 22 may be significantly smaller, especially in cases where the size of the abrasion chamber 12 is relatively large. The distance between the centers of the inlet opening 14 and outlet opening 16 are preferably in the range of 0.15 inches to 5.5 inches, more preferably in the range of 0.3 inches to 2.5 inches and most preferably in the range of 0.4 inches to 1.0 inches. In the embodiment shown, the distance between the openings 14, 16 is approximately 0.7 inches.

Figure 10:
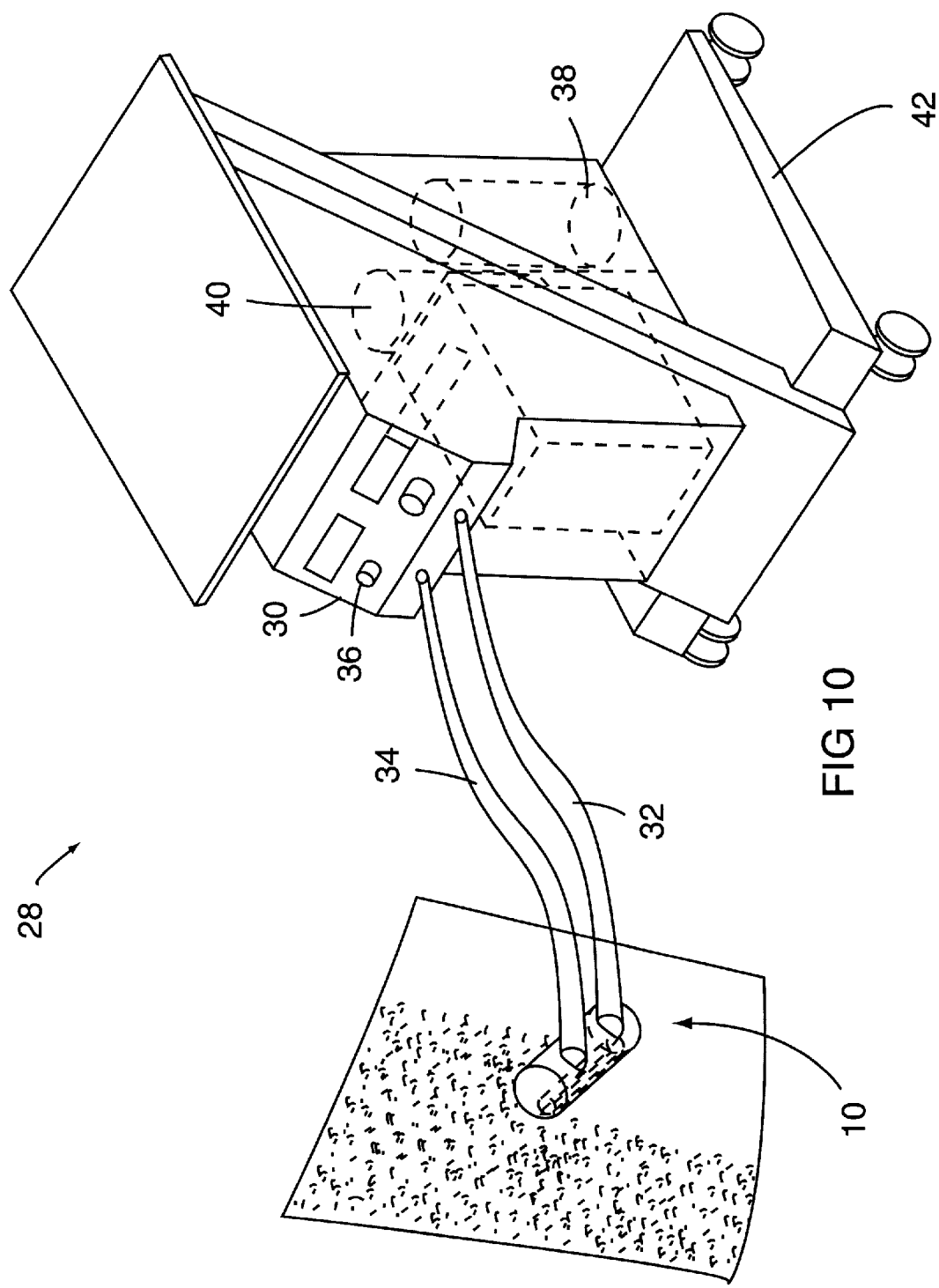
FIG. 10 shows a perspective view of the abrasion nozzle and system in use.

FIG. 10 shows a perspective view of the abrasion nozzle 10 and system 28 in use removing the surface material from an object. In this case, the system 28 is on a wheeled cart 42 allowing the system 28 to move easily to a patient or other object for treatment.

The present invention has been described and shown as a treatment for skin abrasion. However, other uses of the system are possible, for example, abrading hulls of boats and ships, wood, cement, marble, etc. In these other application, other materials may be used, such as the abrasive material currently used for sanding, sand blasting, or otherwise removing surface material from an object. If the device is used for industrial applications, such as cleaning the hull of a ship, then the nozzle would preferably be formed of a more durable long-lasting material in order to last through longer term use. The dimensions given in the specification above are exemplary of a device for dermatological applications. The dimensions would be altered depending on the chosen application. For example, if the device were used for abrading the hull of a ship, the size of the entire device would be significantly increased and/or the relative sizes of the parts may change. For highly sensitive or detailed applications, the size of the device may be reduced.

Many features have been listed with particular configurations, options, and embodiments. Any one or more of the features described may be added to or combined with any of the other embodiments or other standard devices to create alternate combinations and embodiments.

Although the examples given include many specificities, they are intended as illustrative of only a few possible embodiments of the invention. Other embodiments and modifications will, no doubt, occur to those skilled in the art. Thus, the examples given should only be interpreted as illustrations of some of the preferred embodiments of the invention, and the full scope of the invention should be determined by the appended claims and their legal equivalents.

I claim:

1. A skin abrasion system for abrading the surface tissue of a patient, the skin abrasion system comprising:
   an abrasion material source chamber,
   an abrasion nozzle having and elongated slot in a sidewall thereof,
   a material collection chamber,
   a first passage leading from said abrasion material source chamber to said abrasion nozzle,
   a second passage leading from said abrasion nozzle to said material collection chamber,
   and a spiral impelling means for impelling an abrasive material from said abrasion material source chamber to flow in a spiral path within said abrasion nozzle.

2. The skin abrasion system of claim 1 wherein said spiral impelling means is at least one groove on an interior surface of said abrasion nozzle, whereby when the abrasive material impacts said interior surface, said at least one groove urges the abrasive material to move follow a spiral path.

3. The skin abrasion system of claim 1 wherein said abrasion nozzle has an inlet opening, said first passage being in fluid communication with said inlet opening, said inlet opening being at an angle to said slot in said sidewall of said abrasion nozzle, wherein said angle is said spiral impelling means.

4. The skin abrasion system of claim 3 wherein said angle is greater than 0.

5. The skin abrasion system of claim 3 wherein said angle is between approximately 5 and 175 degrees.

6. The skin abrasion system of claim 3 wherein said angle is between approximately 15 and 90 degrees.

7. The skin abrasion system of claim 3 wherein said angle is between approximately 30 and 60 degrees.

8. The skin abrasion system of claim 3 wherein said angle is approximately 45 degrees.

* * * * *